US007601694B2

(12) United States Patent
Brooks et al.

(10) Patent No.: US 7,601,694 B2
(45) Date of Patent: Oct. 13, 2009

(54) CLK-PEPTIDE AND SLK-PEPTIDE

(75) Inventors: Peter C. Brooks, Carmel, NY (US); Jennifer M. Roth, North Babylon, NY (US)

(73) Assignee: New York University, New York, NY (US)

( * ) Notice: Subject to any disclaimer, the term of this patent is extended or adjusted under 35 U.S.C. 154(b) by 490 days.

(21) Appl. No.: 10/782,728

(22) Filed: Feb. 18, 2004

(65) Prior Publication Data

US 2004/0242490 A1 Dec. 2, 2004

Related U.S. Application Data (60) Provisional application No. 60/449,250, filed on Feb. 20, 2003.

(51) Int. Cl.
*A61K 38/10* (2006.01)
(52) U.S. Cl. .................. 514/15; 514/14; 530/327
(58) Field of Classification Search ........................ None
See application file for complete search history.

(56) References Cited

U.S. PATENT DOCUMENTS

| | | | |
|---|---|---|---|
| 5,092,885 A | 3/1992 | Yamada et al. | |
| 5,112,946 A | 5/1992 | Maione | |
| 5,192,744 A | 3/1993 | Bouck et al. | |
| 5,202,352 A | 4/1993 | Okada et al. | |
| 6,071,520 A | 6/2000 | Noteborn et al. | |
| 7,122,635 B2 * | 10/2006 | Brooks et al. ............ | 530/387.1 |
| 2004/0224896 A1 | 11/2004 | Brooks et al. | |

FOREIGN PATENT DOCUMENTS

| | | |
|---|---|---|
| WO | WO 00/40597 | 7/2000 |
| WO | WO-00/40597 A1 | 7/2000 |
| WO | WO-00-59532 A1 | 10/2000 |
| WO | WO-2004-73649 A2 | 2/2004 |

OTHER PUBLICATIONS

Amstutz, et al., In vitro display technologies: novel developments and applications. Current Opinion in Biotechnology 2001;12:400-405.
Engel J, Versatile collagens in invertebrates. Science 1997;277:1785-1786.
Gordon, et al., The contribution of collagenous proteins to tissue-specific matrix assemblies. Current Opinion in Cell Biology 1990;2:833-838.
Green, et al., Proc. Natl. Acad. Sci. USA 2003;100:1010-1015.
Guo, et al., In vitro evolution of amphioxus insulin-like peptide to mammalian insulin. Biochemistry 2002;41:10603-10607.
Hangai, et al., Matrix metalloproteinase-9-dependent exposure of a cryptic migratory control site in collagen is required before retinal angiogenesis. American Journal of Pathology 2002;161(4):1429-1437.
Heeley RP, Endocr. Res. 2002;28:217-229.
Ingham, et al., Type I collagen contains at least 14 cryptic fibronectin binding sires of similar affinity. Archives of Biochemistry and Biophysics 2002;407:217-223.
Liljeblad, et al., Analysis of agalacto-IgG in rheumatoid arthritis using surface plasmon resonance. Glycoconjugate Journal 2000;17:323-329.
Stephanopoulos G, Metabolic engineering by genome shuffling. Nature Biotechnology 2002;20(7):666-668.
Tani, et al., In vitro selection o fibronectin gain-of-function mutations. Biochem. J. 2002;365:287-294.
Steffensen, et al., Human fibronectin and MMp-2 collagen binding domains compete for collagen binding sites and modify cellular activation of MMP-2. Matrix Biology 2002;21:399-414.
Varner, et al., Cell Adh. Commun. 1995;3:367-374.
Xu, et al., Generation of monoclonal antibodies to cryptic collagen sites by using subtractive immunization. Hybridoma 2000;19(5)375-385.
Xu, et al., Proteolytic exposure of a cryptic site within collagen type IV is required for angiogenesis and tumor growth in vivo. Journal of Cell Biology 2001;154(5):1069-1079.
Zhao, et al., Directed evolution of enzymes and pathways for industrial biocatalysis. Current Opinion in Biotechnology 2002;13:104-110.
Akalu, A. et al., "Inhibition of Angiogenesis and Tumor Metastasis by Targeting a Matrix Immobilized Cryptic Extracellular Matrix Epitope in Laminin," Cancer Res. 67(9):4353-4363 (2007).
Auerbach, R. et al., "Angiogenesis Assays: A Critical Overview," Clin. Chem. 49(1):32-40 (2003).
Auerbach, R. et al., "Angiogenesis assays: Problems and pitfalls," Cancer Metastasis Rev. 19:167-172 (2000).
Battegay, E.J., "Angiogenesis: mechanistic insights, neovascular diseases, and therapeutic prospects," J. Mol. Med. 73:333-346 (1995).
Blood, C.H. et al., "Tumor interactions with the vasculature: angiogenesis and tumor metastasis," Biochim. Biophys. Acta. 1032:89-118 (1990).
Brooks, P. et al., "Integrin $\alpha_v\beta_3$ Antagonists Promote Tumor Regression by Inducing Apoptosis of Angiogenic Blood Vessels," Cell 79:1157-1162 (1994).
Brooks, P. et al., "Disruption of Angiogenesis by PEX, a Noncatalytic Metalloproteinase Fragment with Integrin Binding Activity," Cell 92:391-400 (1998).
Brooks, P. et al., "Antiintegrin $\alpha_v\beta_3$ blocks human breast cancer growth and angiogenesis in human skin," J. Clin. Invest. 96:1815-1822 (1995).

(Continued)

*Primary Examiner*—Christopher R. Tate
*Assistant Examiner*—Roy Teller
(74) *Attorney, Agent, or Firm*—Wilson Sonsini Goodrich & Rosati (57) ABSTRACT

The invention describes methods for inhibiting angiogenesis in a tissue by administering an antagonist that specifically binds to a proteolyzed or denatured collagen type-IV with substantially greater affinity than to the native triple helical form of collagen type-IV. Methods utilizing such antagonists for therapeutic treatment of tumor growth, tumor metastasis or of restenosis also are described, as are methods to use such antagonists as diagnostic markers of angiogenesis in normal or diseased tissues both in vivo and ex vivo.

9 Claims, 5 Drawing Sheets

OTHER PUBLICATIONS

Burgess, W.H. et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," J. Cell. Biol. 111:2129-2138 (1990).

Fischer, C., "Principles and Therapeutic Implications of Angiogenesis, Vasculogenesis and Arteriogenesis," HEP 176(11):157-212 (2006).

Gonzalez, A. et al., "Complex interactions between the laminin alpha 4 subunit and integrins egulate endothelial cell behavior in vitro and angiogenesis in vivo," PNAS USA 99(25):16075-16080 (2002).

Guo, H. et al., "Protein tolerance to random amino acid change," PNAS USA 101(25):9205-9210 (2004).

Jo, N. et al., "Inhibitory effect of an antibody to cryptic collagen type IV epitopes on choroidal neovascularization," Mol. Vision 12:1243-1249 (2006).

Jones, D.T., "Critically assessing the state-of-the-art in protein structure prediction," Pharmacogenomics J. 1:126-134 (2001).

Kim, J. et al., "Inhibition of Angiogenesis and Angiogenesis-dependent Tumor Growth by the Cryptic Kringle Fragments of Human Apolipoprotein(a)," J. Biol. Chem. 278:29000-29008 (2003).

Kim, S. et al., "Regulation of Angiogenesis In Vivo by Ligation of Integrin α5β1 with the Central Cell-Binding Domain of Fibronectin," Am. J. Path. 156:1345-1362 (2000).

Kikkawa, Y. et al., "Isolation and characterization of laminin-10/11 secreted by human lung carcinoma cells. Laminin-10/11 mediates cell adhesion through integrin alpha3 beta1," J. Biol. Chem. (online), Am. Soc. Biochem. Mol. Biol., 273 (25):15854-15859 (1998).

Kurkinen, M. et al., "In vitro synthesis of laminin and entactin polypeptides," J. Biol. Chem. 258(10):6543-6548 (1983).

Kurschat, P., "Mechanisms of Metastasis," Clin. Exp. Dermatol. 25:482-489 (2000).

Lazar, E. et al., "Transforming Growth Factor α: Mutation of Aspartic Acid 47 and Leucine 48 Results in Different Biological Activities," Mol. Cell. Biol. 8:1247-1252 (1998).

Liotta, L. A. et al., "Cancer Metastasis and Angiogenesis: An Imbalance of Positive and Negative Regulation," Cell 65:327-336 (1991).

National Cancer Institute, "Radiation Therapy", www.cancer.gov.

Qin, X. et al., "Structure-Function Analysis of the Human Insulin-like Growth Factor Binding Protein-4," JBC 273(36):23509-23516 (1998).

Roskelley, C.D. et al., "A hierarchy of ECM-mediated signalling regulates tissue-specific gene expression," Curr. Op. Cell Biol. 7:736-747 (1995).

Skolnick, J. et al., "From genes to protein structure and function: novel applications of computational approaches in the genomic era," Trends Biotech. 18:34-39 (2000).

Staton, C.A. et al., "Current methods for assaying angiogenesis in vitro and in vivo," Intl J. Exp. Path. 85:233-248 (2004).

Tosatto, S.C.E. et al., "Large-Scale Prediction of Protein Structure and Function from Sequence," Curr. Pharma. Des. 12:2067-2086 (2006).

Weidner, N. et al., "Tumor Angiogenesis: A New Significant and Independent Prognostic Indicator in Early-Stage Breast Carcinoma," J. Natl. Cancer Inst. 84:1875-1887 (1992).

Weidner, N. et al., "Tumor Angiogensis and Metastasis-Correlation in Invasive Breast Carcinoma," N. Engl. J. Med. 324:1-7 (1991).

Wyckoff, J., "A Critical Step in Metastasis: In Vivo Analysis of Intravasation at the Primary Tumor," Cancer Res. 60:2504-2511 (2000).

* cited by examiner

CLK-PEPTIDE AND SLK-PEPTIDE

This application claims priority under 35 U.S.C. §19(e) to U.S. provisional patent application Ser. No. 60/449,250 filed on Feb. 20, 2003. The contents of this provisional application are hereby incorporated by reference in their entirety.

STATEMENT OF FEDERALLY-SPONSORED RESEARCH

The present invention was made with Government support under a contract 2RO1CA91645 awarded by the National Institutes of Health. The United States Government may have certain rights to this invention pursuant to the grant.

FIELD OF THE INVENTION

This invention relates generally to the field of medicine, and more specifically to methods and compositions for inhibiting or detecting angiogenesis, tumor growth and metastases using active agents comprising selective antagonists of denatured collagen type-IV.

BACKGROUND

Tumor growth and metastasis impact a large number of people each year. It is estimated that over 600,000 new cases of cancer will be diagnosed in the United States per year (Varner, J., et al., Cell Adh. Commun. 1995; 3:367-374).

Metastasis, the spread of malignant tumor cells from the primary tumor mass to distant sites involves a complex series of interconnected events. (Liotta, et al., Cell 1991; 64:327-336; Wyckoff, et al., Cancer Res. 2000; 60:2504-2511; Kurschat, et al., Clinc. Exp. Dermatol. 2000; 25:482-489.) The metastatic cascade is initiated by a series of genetic alterations leading to changes in cell-cell interaction, which allow tumor cells to dissociate from the primary tumor mass. The dissociated cells locally invade and migrate through proteolytically modified extracellular matrix (ECM). The dissociated cells gain access to the circulatory system. To establish a metastatic deposit, the circulating tumor cells must evade host immune defenses, arrest in the microvasculature, and extravasate out of the circulation. The tumor cells then invade the ECM at the new site, proliferate, induce angiogenesis, and continue to grow.

Therapies designed to block angiogenesis may significantly effect the growth of solid tumors and metastases. Blocking tumor neovascularization significantly inhibits tumor growth in various animal models, and human clinical data is beginning to support this contention as well (Varner, J., et al., Cell Adh. Commun. 1995; 3:367-374). These and other studies suggest that the growth of solid tumors requires new blood vessel growth for continued expansion of the tumors beyond a minimal size (Varner et al., 1995; Blood, C. H., et. al., Biochim. Biophys. Acta. 1990; 1032:89-118; Weidner, N. et al. J Natl. Cancer Inst. 1992; 84:1875-1887; Weidner, N. et al., N. Engl. J Med. 1991; 324:1-7; Brooks, P. C. et al. J Clin. Invest. 1995; 96:1815-1822; Brooks, P. C. et al., Cell 1994; 79:1157-1164; Brooks, P. C. et al. Cell 1996; 85:683-693; Brooks, P. C. et al., Cell 1998; 92:391-400). Inhibition of angiogenesis is, therefore, a promising treatment for cancer and metastatic disease.

Angiogenesis is the physiological process by which new blood vessels develop from pre-existing vessels (Varner et al., 1995; Blood et al., 1990; Weidner et al., 1992). This complex process requires cooperation of a variety of molecules including growth factors, cell adhesion receptors, matrix degrading enzymes and extracellular matrix components (Varner et al., 1995; Blood et al., 1990; Weidner et al., 1992).

Inhibition of angiogenesis may also be useful in treating other diseases that are characterized by unregulated blood vessel development including, for example, ocular diseases (e.g., macular degeneration and diabetic retinopathy) and inflammatory diseases (e.g., arthritis and psoriasis) (Varner et al., 1995).

Many investigators have focused their anti-angiogenic approaches towards growth factors and cytokines that initiate angiogenesis (Varner et al., 1995; Blood et al., 1990; Weidner et al., 1992; Weidner et al., 1991; Brooks et al., 1995; Brooks et al., 1994; Brooks et al., 1997). There are, however, a large number of growth factors and cytokines that have the capacity to stimulate angiogenesis. The therapeutic benefit of blocking a single cytokine, therefore, may have only limited benefit due to this redundancy. Little attention has been directed to other anti-angiogenic targets.

Recent studies have suggested that angiogenesis requires proteolytic remodeling of the extracellular matrix (ECM) surrounding blood vessels in order to provide a microenvironment conducive to new blood vessel development (Varner et al. (1995); Blood et al. (1990); Weidner et al. (1992); Weidner et al. (1991); Brooks et al. (1995); Brooks et al. (1994); Brooks et al. (1997)). The extracellular matrix protein collagen makes up over 25% of the total protein mass in animals and the majority of protein within the ECM.

Inhibition of angiogenesis would be a useful therapy for restricting tumor growth and metastases. Inhibition of angiogenesis may be effected by (1) inhibition of release of "angiogenic molecules" such as, for example, bFGF (basic fibroblast growth factor), (2) neutralization of angiogenic molecules, (e.g., anti-bFGF antibodies), and (3) inhibition of endothelial cell response to angiogenic stimuli. (Folkman et al., Cancer Biology, 3:89-96 (1992)). Several potential endothelial cell response inhibitors have been described that might be used to inhibit angiogenesis, e.g., collagenase inhibitors, basement membrane turnover inhibitors, angiostatic steroids, fungal-derived angiogenesis inhibitors, platelet factor 4, thrombospondin, arthritis drugs such as D-penicillamine and gold thiomalate, vitamin D3 analogs, and alpha-interferon. Additional proposed inhibitors of angiogenesis have also been described in the literature. (Blood, et al. (1990); Moses et al. (1990) Science 248:1408-1410; Ingber, et al. (1988) Lab. Invest., 59:44-5 1; and U.S. Pat. Nos. 5,092,885; 5,112, 946; 5,192,744; and 5,202,352.)

Collagen is an extracellular matrix protein containing a [Gly-Xaa-Xaa]$_n$ sequence motif. Collagen types are well known in the art (see, e.g., Olsen, B. R. (1995) Curr. Op. Cell. Biol. 5:720-727; Kucharz, E. J. The Collagens: Biochemistry and Pathophysiology. Springer-Verlag, Berlin, 1992; Kunn, K. in Structure and Function of Collagen Types, eds. R. Mayne and R. E. Burgeson, Academic Press, Orlando). Collagen is a fibrous multi-chain triple helical protein that exists in numerous forms (Olsen, B. R. (1995) Curr. Opin. Cell Biol 7, 720-727; Van der Rest, M., et al. (1991) FASEB 5, 2814-2823). At least 18 genetically distinct types of collagen have been identified, many of which have distinct tissue distributions and functions (Olsen (1995); Van der Rest, et al. (1991)). Collagen type-I is the most abundant collagen in the extracellular matrix. Collagen type-I, collagen type-III, collagen type-IV and collagen type-V have been shown to be associated with all pre-existing blood vessels in vivo.

The mature collagen molecule is composed of two α1 chains and one α2 chain twisted into a triple helix. Collagens type-I and type-IV, for example, are composed of major chains designated α1(I) and α2(I) and α1(IV) and α2(IV), respectively. In vivo, collagen is normally found in the mature triple helical form.

Denaturation of the native three dimensional structure of mature triple helical collagen may expose cryptic regulatory regions that control angiogenesis. Disruption by antibodies of cellular interactions with denatured collagen type-IV blocks tumor growth and angiogenesis (Xu, J., et al. (2001) J. Cell Biol. Vol. 154:1069-1079; Hangia, et al. (2002) Am. J. Pathol. Vol. 161:1429-1437). Brooks et al. (PCT WO 00/40597) discloses antibodies that bind to cryptic regions within various denatured collagen types.

It has now been surprisingly discovered that peptide antagonists selective for denatured collagen type-IV inhibit angiogenesis and tumor growth. Peptide antagonists that specifically bind to denatured collagen type-IV provide the basis for powerful new compounds for treating cancer, inflammatory diseases and other angiogenesis-associated diseases.

SUMMARY OF THE INVENTION

The invention provides a method for inhibiting angiogenesis, tumor growth and metastasis in the tissue of a mammal by administering to the mammal an active agent comprising an angiogenesis-inhibiting amount of a selective antagonist of denatured collagen type-IV.

The invention also provides a method for inhibiting tumor growth and metastasis in the tissue of a mammal by administering to the mammal an active agent comprising a tumor cell adhesion-inhibiting amount of a selective antagonist of denatured collagen type-IV.

The present invention also provides peptide antagonists that specifically bind to denatured collagen type-IV and can be used to inhibit angiogenesis, tumor growth and metastasis in mammals. More specifically, the invention provides biologically active agents comprising denatured collagen type-IV selective antagonists that inhibit angiogenesis, tumor growth and metastasis. The binding affinity of the peptide antagonists of the present invention to denatured collagen type-IV is substantially greater than the binding affinity of the antagonists to native forms of collagen type-IV.

The denatured collagen type-IV selective antagonists for use in the present invention have a core amino acid sequence L-K-Q-N-G-G-N-F-S-L [(SEQ ID NO: 1)].

A preferred denatured collagen type-IV selective antagonist for use in the present invention is a peptide having the amino acid sequence NH$_2$-C-L-K-Q-N-G-G-N-F-S-L-G-COOH (CLK-peptide) [(SEQ ID NO: 2)].

Another preferred denatured collagen type-IV selective antagonist for use in the present invention is a peptide having the amino acid sequence NH$_2$-S-L-K-Q-N-G-G-N-F-S-L-C-COOH (SLK peptide) [(SEQ ID NO: 3)].

Another preferred denatured collagen type-IV selective antagonist for use in the present invention is a peptide having the amino acid sequence NH$_2$—K-G-G-C-L-K-Q-N-G-G-N-F-S-L-G-G-K-A-COOH (KGGCLK peptide) [(SEQ ID NO: 4)].

In another embodiment of the invention, the denatured collagen type-IV selective antagonist is conjugated to a cytotoxic or cytostatic agent.

In another aspect, the invention provides methods for detecting angiogenesis in a mammalian tissue by exposing the tissue to a detectably labeled denatured collagen type-IV selective antagonist.

In a still further embodiment, the invention includes a method for detecting tumorous tissue, metastases, tumor invasion, bacterial invasion, arthritis, inflammation or any other disease or condition that is characterized or associated with denaturation of collagen type-IV in a mammalian tissue by exposing the tissue to be tested to a detectably labeled denatured collagen type-IV selective antagonist.

BRIEF DESCRIPTION OF THE FIGURES

FIGS. 3(a), (b), and (c) depict a chick chorioallantoic membrane (CAM) without bFGF-induced angiogenesis, a CAM following bFGF-induced angiogenesis, and a CAM treated with CLK-peptide after bFGF-induced angiogenesis.

DETAILED DESCRIPTION OF THE INVENTION

The present invention provides compositions and methods for inhibiting angiogenesis, tumor growth, metastasis, bacterial invasion, arthritis, inflammation or any other disease or condition that is characterized or associated with denaturation of collagen type-IV in mammals and for detecting angiogenesis, tumor growth, metastasis, bacterial invasion, arthritis, inflammation or any other disease or condition that is characterized or associated with denaturation of collagen type-IV in mammalian tissue through the use of denatured collagen type-IV selective antagonists. Peptides having the amino acid core L-K-Q-N-G-G-N-F-S-L selectively bind denatured collagen type-IV.

The methods of the present invention provide biologically active agents that inhibit the formation of new blood vessels required to establish and sustain cancer cells. Additionally, the present invention provides methods and compositions that directly inhibit tumor growth, metastasis, inflammation, and other diseases or conditions associated with cellular interactions with denatured collagen type-IV. The active agents of the present invention selectively bind to denatured collagen type-IV thereby preventing angiogenesis, tumor growth, metastasis, arthritis, inflammatory diseases and other diseases or conditions associated with cellular interactions with such collagen.

Definitions

As used herein, the term "angiogenesis" includes a variety of processes involving neovascularization of a tissue including "sprouting", vasculogenesis, or vessel enlargement, all of which angiogenesis processes involve disruption of extracellular matrix collagen in blood vessels. Angiogenesis that takes place during traumatic wound healing, corpus leuteum formation and embryogenesis is a part of normal physiology. The majority of angiogenesis cases, however, are associated with disease processes.

As used herein, "antagonist" refers to a compound that inhibits a naturally occurring biological activity.

As used herein, a "cryptic epitope" within a collagen is a sequence that is not exposed for recognition within a native collagen, but is capable of being recognized by an antagonist of a denatured collagen. Peptide sequences that are not solvent exposed or are only partially solvent exposed in the native structure are potential cryptic epitopes. The sequence of cryptic epitopes can be identified by determining the specificity of an antagonist. Candidate cryptic epitopes also can be identified, for example, by examining the three dimensional structure of a native triple helical collagen.

As used herein "native collagen" refers to collagen that is predominantly in its triple helical form.

As used herein "denatured collagen" refers to collagen that is no longer predominantly in its native triple helical form. The denatured collagen can be denatured full-length collagen or a fragment of collagen. A fragment of collagen can be any collagen sequence shorter than a full length collagen sequence. For fragments of collagen with substantial native structure, denaturation can be effected as for a native full-length collagen. Fragments also can be of a size such that they do not possess significant native structure or possess regions without significant native triple helical form. The term "denatured collagen" encompasses "proteolyzed collagen". "Proteolyzed collagen" refers to a collagen that has been structurally altered through the action of a proteolytic enzyme.

As used herein, a "denatured collagen type-IV selective antagonist" is a substance that has a substantially greater binding affinity to denatured collagen type-IV than to native collagen type-IV.

As used herein, an "epitope" is that amino acid sequence or sequences that are recognized by an antagonist of the invention. An epitope can be a linear peptide sequence or can be composed of noncontiguous amino acid sequences. An antagonist can recognize one or more sequences, therefore an epitope can define more than one distinct amino acid sequence target. The epitopes recognized by an antagonist can be determined by peptide mapping and sequence analysis techniques well known to one of skill in the art.

The term "peptide" as used herein refers to a series of two or more covalently linked amino acids. A linear, cyclic, or branched peptide can be used in practicing the invention.

The term "core amino acid sequence" as used herein refers to a sequence of amino acids that can begin at the N-terminus of a peptide, can be an internal sequence in a peptide, or can end at the C-terminus of a peptide.

As used herein, the term "peptido-mimetic" is used to refer to compounds that mimic the activity of a peptide. Peptido-mimetics are non-peptides but may comprise amino acids linked by non-peptide bonds. In a peptido-mimetic, the three dimensional structure of a peptide that specifically interacts with the three dimensional structure of a cryptic epitope is duplicated by a molecule that is not a peptide.

"Neovascularization" as used herein means the development of new blood vessels. Neovascularization may refer to the process of angiogenesis and/or to the result of angiogenesis, which is new blood vessel formation.

As defined herein, a "patient" is any mammal in which treatment of angiogenic diseases, tumor growth or metastasis is desirable. Preferred patients include agricultural or domestic mammals; for example, a pig, a cow, a horse, a goat, a sheep, a mule, a donkey, a dog, a cat, a rabbit, a mouse, or a rat. An especially preferred patient is a human.

The phrase "pharmaceutically acceptable" refers to molecular entities and compositions that are "generally regarded as safe", e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

"Substantially greater affinity" means a binding affinity at least 1.5-fold greater for the target compound as compared to the standard compound and, more preferably, at least 10-fold greater and, most preferably, at least 100-fold greater. The selective antagonists are specific for denatured collagen type-IV (the target compound) and the binding affinities of the selective antagonists are compared to native collagen (the standard compound). Apparent binding affinity measurements can be made using enzyme linked immunosorbent assay (ELISA) or other techniques familiar to one of skill in the art, e.g., surface plasmon resonance technique (analyzed on a BIOCORE 2000 system) (Liljeblad, et al. (2000) Glyco. J., Vol. 17: 323-329), and standard measurements and traditional binding assays (Heeley, R. P. (2002) Endocr. Res., Vol. 28: 217-229).

A "therapeutically effective amount" is an amount of selective denatured collagen antagonist sufficient to produce a measurable decrease in angiogenesis in the tissue being treated, i.e., an angiogenesis-inhibiting amount; or an amount of selective denatured collagen antagonist sufficient to produce a measurable decrease in tumor growth, metastasis, arthritis, inflammatory disease or condition associated denatured collage type-IV.

The term "treatment" is used herein to mean the administration of a denatured collagen type-IV selective antagonist to prevent angiogenesis, tumor growth, metastasis, bacterial invasion, arthritis, inflammation or any other disease or condition that is characterized or associated with denaturation of collagen type-IV or to inhibit the progression of pre-existing angiogenesis, tumor growth, metastasis, bacterial invasion, arthritis, inflammation or any other disease or condition that is characterize or associated with denaturation of collagen type-IV in a patient with such a disease or condition, and/or to ameliorate symptoms associated with such diseases or conditions.

The term "unit dose" when used in reference to a therapeutic composition of the present invention refers to a physically discrete unit suitable as a unitary dosage for the subject, each unit containing a predetermined quantity of active material calculated to produce the desired therapeutic effect either alone or in a composition comprising a suitable diluent; carrier, vehicle, or other excipient.

Denatured Collagen Type-IV Antagonists

The biologically active agents of the present invention comprise compounds that have a strong binding affinity for denatured collagen type-IV. A denatured collagen type-IV selective antagonist of the present invention has the amino acid core sequence L-K-Q-N-G-G-N-F-S-L.

One preferred denatured collagen type-IV selective antagonist for use in the present invention is CLK-peptide. CLK-peptide binds to denatured collagen type-IV with high specificity. The amino acid sequence of CLK peptide is NH2-C-L-K-Q-N-G-G-N-F-S-L-G-COOH. The CLK-peptide binds to regions within denatured collagen type-IV and inhibits cellular interactions with denatured collagen type-IV. Adhesive cellular interactions with functional epitopes within the extracellular matrix have a role in regulating angiogenesis, tumor growth and metastasis in vivo. (Xu, J., et al. (2001) J. Cell Biol. Vol. 154:1069-1079; Hangia, et al. (2002) Am. J. Pathol. Vol. 161:1429-1437). CLK-peptide has been shown to potently block angiogenesis (Example 4 below) and tumor growth and metastasis (Example 5 below) in vivo.

Another preferred selective denatured collagen type-IV antagonist for use in the present invention is SLK-peptide. SLK-peptide binds with high specificity to denatured collagen type-IV and inhibits cellular interactions with denatured collagen type-IV. The amino acid sequence of SLK-peptide is NH2-S-L-K-Q-N-G-G-N-F-S-L-C-COOH.

A further preferred selective denatured collagen type-IV antagonist for use in the present invention is KGGCLK peptide. KGGCLK peptide binds with high specificity to denatured collagen type-IV and inhibits cellular interactions with denatured collagen type-IV. The amino acid sequence of KGGCLK peptide is $NH_2$—K-G-G-C-L-K-Q-N-G-G-N-F-S-L-G-G-K-COOH.

Sequential solid phase binding assays, for example, can be used to identify denatured collagen type-IV selective antagonists. Preferred methods for identifying denatured collagen type-IV antagonists are subtractive immunization (Xu, J. et al. (2000) Hybridoma, Vol. 19:375-385) and subtractive phage display (Example 1) (Amstutz P., et al. (2001) Curr. Opin. Biotechnol., vol. 12:400-405).

A preferred method of denaturation is thermal denaturation because thermal denaturation results in fewer small fragments that may have little immunogenicity in vivo. Collagen type-IV can be thermally denatured by, for example, heating collagen type-IV to 100° C. for fifteen minutes. Denaturation can also be accomplished by treating the collagen with a chaotropic agent. Suitable chaotropic agents include, for example, guanidinium salts. Collagen can also be denatured by ionizing radiation, non-ionizing radiation (ultraviolet), thermal injury, and mechanical stress or force. Collagen can be denatured by proteolysis. In particular, proteolyzed collagen can be prepared by treating the collagen with a metalloproteinase, such as MMP-1, MMP-2 or MMP-9, or by treating the collagen with a cellular extract containing collagen degrading activity. Proteolyzed collagen may also occur naturally at sites of neovascularization, tumor growth, metastasis, bacterial invasion, arthritis and inflammation in a tissue.

Denaturation of a collagen can be monitored, for example, by spectroscopic changes in optical properties such as absorbance, circular dichroism or fluorescence of the protein, by nuclear magnetic resonance, by Raman spectroscopy, or by any other suitable technique.

The resultant denatured collagen type-IV fragments can then be fixed to a solid matrix. Peptides known to bind collagen can be obtained from a peptide library. (Amstutz P., et al. (2001) Curr. Opin. Biotechnol., vol. 12:400-405). The collagen-binding peptides can be passed over the solid matrix. Peptides that bind denatured collagen type-IV adhere to the solid matrix. The adherent peptides can then be washed from the solid matrix and then passed over a second solid matrix to which native collagen type-IV is fixed. Peptides that do not bind to the second solid matrix are denatured collagen type-IV selective antagonists.

The selective peptide and polypeptide antagonists used in the present invention can be generated using several different techniques that are well known to those skilled in the art. For example, a two hybrid system (e.g., Fields, S. (1989) Nature 340:245-6) uses a collagen fragment as "bait" for selecting protein antagonists from a library that binds to the collagen peptide. This system and its operation are described in Green, D. M., et al., Proc. Natl. Acad. Sci. USA. 100:1010-1015 (2003) and in Gyuris, J. et al. (1993) Cell, Vol. 75: 791-803. The library of potential antagonists can be derived from a cDNA library, for example. In another embodiment, the potential antagonists can be variants of known collagen binding proteins such as integrins and fibronectin. (Hynes, R. O. (1992) Cell, Vol. 69:11-25; Steffensen, B., et al. (2002) Matrix Biol., Vol. 21:399-414; Ingham, K. C., et al. (2002) Arch. Biochem. Biophys., Vol. 407:217-223) Such proteins can be randomly mutagenized or subjected to gene shuffling, or other well known techniques for generating sequence diversity (Tani, P. H., et al. (2002) Biochm. J., Vol. 365:287-294; Stephanopoulos, G. (2002) Nat. Biotechnol., Vol. 20:666-668).

Peptide antagonists of the invention also can be generated using molecular evolution techniques as disclosed in Zhao, H., et al. (2002) Cur. Opin. Biotechnol., Vol. 13:104-110 and Guo, Z., et al. (2002) Biochemistry, Vol. 41:10603-10607. Libraries of proteins can be generated by mutagenesis, gene shuffling or other well known techniques for generating molecular diversity. Protein pools representing numerous variants can be selected for their ability to bind to denatured collagen, for instance, by passing such protein pools over a solid matrix to which a denatured collagen has been attached. Elution with gradients of salt, for example, can provide purification of variants with affinity for the denatured collagen. A negative selection step also can be included whereby such pools are passed over a solid matrix to which native collagens have been attached. The filtrate will contain those variants within the pool that have a reduced affinity for the native form of the collagen.

The peptide and polypeptide antagonists of the present invention also can be generated by phage display. Phage display is a selection technique in which a peptide is expressed as a fusion with a coat protein of a bacteriophage. The result is that the fused protein is displayed on the surface of the virion and the DNA encoding the fusion protein resides within the virion. (Smith G. P. (1985) Filamentous fusion phage: Novel expression vectors that display cloned antigens on the virion surface. Science. 228:1315-1317; Smith G. P., et al. (1993) Libraries of peptides and proteins displayed on filamentous phage. Methods Enzymol. 217:228-257) Phage display allows for rapid identification of peptide ligands for a variety of target molecules using an in vitro process called panning. Panning is carried out, for example, by incubating a library of phage-displayed peptides with a microtiter plate coated with the target, washing away the unbound phage, and eluting the bound phage. The eluted phage is then amplified and taken through additional binding/amplification cycles to enrich the pool in favor of binding sequences. After 3-4 rounds of panning, individual clones are identified by DNA sequencing.

A randomized peptide or protein can be expressed on the surface of a phagemid (a term for the combination of phage and plasmid) particle as a fusion with a phage coat protein. Techniques of monovalent phage display are widely available (see, e.g., Lowman H. B. et al. (1991) Biochemistry 30:10832-8.) Phage expressing randomized peptide or protein libraries can be panned with a solid matrix to which a native collagen molecule has been attached. Remaining phage do not bind native collagens, or bind native collagens with substantially reduced affinity. The phage are then panned against a solid matrix to which a denatured collagen has been attached. Bound phage are isolated and separated from the solid matrix by either a change in solution conditions or, for a suitably designed construct, by proteolytic cleavage of a linker region connecting the phage coat protein with the randomized peptide or protein library. The isolated phage can be sequenced to determine the identity of the selected antagonist.

The well known ELISA assay can be used to identify collagen type-IV selective antagonists for use in practicing the present invention.

A peptide or polypeptide can be identified as an antagonist through the use of a solid phase ELISA to determine whether the peptide or polypeptide binds to denatured or native collagens. The ELISA assay is useful with a variety of collagen types; for example, the ELISA assay can be used with collagen types, I, II, III, IV and V, as well as for other extracellular matrix components. The level of binding affinity can be determined by surface plasmon resonance technique (analyzed on a BIACORE 2000 system) (Liljeblad, et al. (2000) Glyco. J., vol. 17:323-329) and standard measurements by traditional scatchard binding assays (Heeley, R. P. (2002) Endocr. Res., Vol. 28:217-229).

Solid phase ELISA also can be used to identify compounds which exhibit specificity for denatured, but not native, forms of collagen. The specificity assay is conducted by running parallel ELISAs where a potential antagonist is screened concurrently in separate assay chambers for the ability to bind denatured and native collagens.

Antagonists can also be identified by their ability to bind to a solid matrix containing a denatured collagen. Putative antagonists are collected after altering solution conditions, such as salt concentration, pH, temperature, etc. The putative antagonists are further identified by their ability to pass through, under appropriate solution conditions, a solid matrix to which a native collagen has been affixed.

The antagonists of the present invention can be used with collagen type-IV molecules from any invertebrate or vertebrate animal, including humans. Examples of collagen type-IV molecules are found in Engel, J. (1997) Science, Vol. 277:1785-1786 and Gordon, M. K., et al., (1990) Curr. Opin. Cell Biol., Vol. 2:833-838. Preferably, the collagen type-IV is a mammalian collagen type-IV. More preferably, the mammal is a pig, cow, goat, rabbit, mouse, rat, dog, cat, sheep, donkey, horse, or mule. In a particularly preferred embodiment, the collagen is human collagen type-IV.

The active agents for use in the invention comprise one or more denatured collagen type-IV antagonists. An antagonist of denatured collagen type-IV can be any peptide, polypeptide or peptido-mimetic that has substantially greater binding affinity to denatured collagen type-IV than to the native form of collagen type-IV. The peptide antagonists of the present invention may be modified, for example, by phosphorylation, hydroxylation or methylation. Additional modifications that may enhance activity include peptide cyclization and peptide stabilization.

In another embodiment; the present invention includes analogs, fragments, or chemical derivatives of a polypeptide whose amino acid residue sequence is shown herein so long as the peptide is an antagonist of denatured collagen type-IV, but not of native collagen. Therefore, a peptide can be subject to various changes, substitutions, insertions, and deletions where such changes provide for certain advantages in its use. In this regard, a denatured collagen type-IV antagonist peptide of this invention includes the sequence of a recited peptide where one or more sequence changes are made and the peptide retains the ability to function as a denatured collagen type-IV selective antagonist in one or more of the assays as defined herein.

KGGCLK-peptide is one such modified peptide. KGGCLK-peptide is CLK-peptide with sequence KGG added to the N-terminus and GKA added to the C-terminus. The coupling of the amino acids may be accomplished by techniques familiar to those in the art and provided, for example, in Stewart and Young, 1984, Solid Phase Synthesis, Second Edition, Pierce Chemical Co., Rockford, Ill.

The antagonist can be conjugated with cytotoxins such as cisplatin, vinblastine and gemcitabine, for delivery to a tumor or other tissue undergoing angiogenesis, tumor growth, metastasis, arthritis or other disease or condition associated with cellular interactions with denatured collagen type-IV. Such conjugates can be made with a cytolysin or an exotoxin, for example ricin A, diphtheria toxin A, or Pseudomonas exotoxin and fragments thereof. The cytotoxic agent can also be radioactively labeled with an isotope so as to locally deliver a toxic dose of radioactivity to an angiogenic tissue, tumor growth, metastasis or other tissue undergoing cellular interaction with denatured collagen type-IV.

The antagonist can be conjugated with a cytostatic agent such as an anti-angiogenic compound, for delivery to a tumor or other tissue undergoing angiogenesis, tumor growth, metastasis, arthritis or other disease or condition associated with cellular interactions with denatured collagen type-IV. A preferred cytostatic agent is a matrix metalloproteinase (MMP) inhibitor. A preferred MMP inhibitor is Marimistat (British Biotech, Oxford, United Kingdom).

In Vivo Assays for Angiogenesis Inhibition

The selective peptide antagonists of the present invention can be assayed for their ability to modulate angiogenesis in a tissue. Any suitable assay known to one of skill in the art, such as the chick chorioallantoic membrane (CAM) assay, or the rabbit eye assay, or the chimeric mouse assay can be used to monitor such effects. Several non-limiting techniques are described herein.

One angiogenesis assay measures angiogenesis in the chick chorioallantoic membrane (CAM) and is referred to as the CAM assay. The CAM assay is well known among those of ordinary skill in the art and has been used to measure both angiogenesis and neovascularization of tumor tissues (Ausprunk et al., Am. J. Pathol., 79:597-618 (1975) and Ossonski et al., Cancer Res., 40:2300-2309 (1980)).

During the CAM assay, angiogenesis of whole tissue is occurring. The assay measures growth of chick embryo blood vessels into the CAM or into the tissue grown on the CAM. Accordingly, the CAM assay is a valid model for in vivo angiogenesis.

The CAM assay measures inhibition of angiogenesis based on both the amount and extent of new vessel growth. It is furthermore possible to monitor the growth of any tissue transplanted upon the CAM, such as a tumor tissue.

Finally, the CAM assay is particularly useful because there is an internal control for toxicity in the assay system. During the assay a viable, developing chick embryo is exposed to test reagent. The health of the embryo is an indication of toxicity.

In another assay, angiogenesis is measured in an in vivo rabbit eye model, referred to as the "rabbit eye assay". The rabbit eye assay is well known among those of ordinary skill in the art and has been used to measure both angiogenesis and neovascularization in the presence of angiogenic inhibitors such as thalidomide. (D'Amato et al. (1994) Proc. Natl. Acad. Sci. 91:4082-4085).

The rabbit eye assay is a well recognized assay model for in vivo angiogenesis because angiogenesis, exemplified by rabbit blood vessels growing from the rim of the cornea into the cornea, is easily visualized through the naturally transparent cornea of the eye. Additionally, both the extent and the amount of stimulation or inhibition of angiogenesis, or regression of angiogenesis, can easily be monitored over time.

The rabbit is exposed to any test reagent used, and therefore the health of the rabbit is an indication of toxicity of the test reagent.

Another assay measures angiogenesis in a chimeric mouse: human model and is referred to as the chimeric mouse assay. (Yan, et al. (1993) J Clin. Invest. 91:986-996). The chimeric mouse assay is a useful assay model for in vivo angiogenesis because the transplanted skin grafts closely resemble normal human skin histologically and neovascularization of whole tissue is occurring wherein actual human blood vessels are growing from the grafted human skin into the human tumor tissue on the surface of the grafted human skin. The origin of the neovascularization into the human graft can be demonstrated by immunohistochemical staining of the neovasculature with human-specific endothelial cell markers.

The chimeric mouse assay demonstrates regression of neovascularization based on both the amount and extent of regression of new vessel growth. Furthermore, effects on the growth of any tissue transplanted upon the grafted skin, such as a tumor tissue, may be monitored. Finally, the assay is useful because there is an internal control for toxicity in the assay system. The chimeric mouse is exposed to any test reagent used, and therefore the health of the mouse is an indication of toxicity.

Disease Treatment

The present invention relates generally to the discovery that binding of certain epitopes of denatured collagen type-IV, but not of native collagen type-IV, to selective antagonists inhibits angiogenesis, tumor growth, metastasis, arthritis, and other conditions or diseases associated with cellular interactions with denatured collagen type-IV in the tissues of mammals, including humans and other animals. Angiogenesis is required in a variety of disease processes. By inhibiting angiogenesis, one can intervene in the disease, ameliorate the symptoms, and in some cases cure the disease.

Where the growth of new blood vessels is required to support growth of abnormal tissue, inhibition of angiogenesis will reduce the blood supply to the tissue and thereby contribute to reduction in tissue mass based on blood supply requirements. Examples include growth of tumors, where neovascularization is a continual requirement in order that the tumor grow beyond a few millimeters in thickness, and for the establishment of solid tumor metastases. Where the growth of new blood vessels is the cause of, or contributes to, the pathology associated with a disease, inhibition of angiogenesis will reduce the deleterious effects of the disease. Examples include psoriasis, rheumatoid arthritis, diabetic retinopathy, inflammatory diseases, restenosis, macular degeneration and the like.

The methods of the present invention are effective in part because the therapy is highly selective for angiogenesis and other processes involving cellular interaction with denatured type-IV collagen, and not other biological processes. The discovery that binding of denatured collagens alone can effectively inhibit angiogenesis and other processes involving cellular interaction with denatured type-IV collagen allows for the development of therapeutic compositions with potentially high specificity, and therefore relatively low toxicity.

The present method for inhibiting angiogenesis in a tissue and, therefore, for practicing the methods for treatment of angiogenesis-related diseases, comprises administering to a patient in need of angiogenic treatment a composition comprising a therapeutically effective amount of a denatured collagen type-IV selective antagonist capable of binding selectively to denatured or proteolyzed collagen type-IV, compared to binding native collagen type-IV. Thus, the method comprises administering to a patient a therapeutically effective amount of a pharmaceutical composition comprising a denatured collagen type-IV selective antagonist of the invention.

The invention provides a method for inhibiting angiogenesis, tumor growth, metastasis, arthritis, inflammatory diseases and other diseases or conditions associated with cellular interactions with denatured collagen-type-IV in the tissue of an animal in need of such treatment, including mammals and humans, and, thereby, inhibiting events in the tissue which depend upon angiogenesis. Generally, the method comprises administering to an animal a composition comprising an effective angiogenesis-inhibiting amount of a denatured collagen type-IV selective antagonist.

The present invention also provides a method for inhibiting tumor neovascularization by inhibiting tumor angiogenesis. In certain embodiments, the tissue to be treated is a tumor tissue of a patient with a solid (malignant) tumor, a metastases, a skin cancer, a breast cancer, a hemangioma or angiofibroma and the like cancer; and the angiogenesis to be inhibited is tumor tissue angiogenesis where there is neovascularization of a tumor tissue. Typical solid tumor tissues treatable by the present methods include lung, pancreas, breast, colon, laryngeal, ovarian, Kaposi's sarcoma and similar tissues.

Inhibition of tumor tissue angiogenesis is a significant development because of the important role neovascularization plays in tumor growth. In the absence of neovascularization, tumor tissue does not obtain the required nutrients, slows in growth, ceases additional growth, regresses and ultimately becomes necrotic resulting in killing or eliminating the tumor. An additional significant development is the direct inhibition of tumor growth and metastasis by blocking tumor cell adherence to denatured collagen type-IV and, thereby, preventing the tumor cell from becoming established in the tissue.

The invention also embodies a method of inhibiting tumor growth by preventing angiogenesis in the tumor.

In another aspect, the invention provides methods for inhibiting tumor growth and the formation of metastases through administration of biologically active compositions comprising antagonists of denatured collagen type-IV. These methods are particularly effective because (1) formation of metastases requires denaturation of collagen and vascularization of a primary tumor so that the metastatic cancer cells can exit the primary tumor and (2) establishment of a tumor in a secondary site requires denaturation of collagen and neovascularization to support growth of the metastases.

Additionally, the invention provides methods for inhibiting tumor growth and metastasis by directly inhibiting tumor cell interaction with denatured collagen type-IV. A tumor cell must adhere to a tissue in order to establish itself in the tissue and, subsequently, grow. The methods and compositions of the present invention directly inhibit tumor cell adherence to tissue by blocking tumor cell interaction with denatured collagen type-IV.

In further embodiments, the invention enables any of the foregoing methods to be carried out in combination with other therapies such as, for example, chemotherapy directed against solid tumors. An angiogenesis inhibitor may be administered to a patient in need of such treatment before, during, or after chemotherapy. Preferably an angiogenesis inhibitor is administered to a patient after a regimen of chemotherapy. At such time, the tumor tissue responds to the toxic assault by inducing angiogenesis in order to recover by the provision of blood and nutrients to the tumor tissue. It is also preferred to administer an angiogenesis inhibitor to a patient as a prophylaxis against metastases after surgery on the patient for the removal of solid tumors.

Accordingly, the methods of inhibiting tumor growth, metastasis, and neovascularization disclosed in this application can be applied to inhibit tumor tissue growth, to inhibit tumor metastases formation, and to cause regression of established tumors.

There are a variety of diseases besides cancer in which angiogenesis is believed to be important. These are referred to as angiogenic diseases, including but not limited to, inflammatory disorders such as immune and non-immune inflammation, chronic articular rheumatism and psoriasis; disorders associated with inappropriate or inopportune invasion of vessels such as diabetic retinopathy, neovascular glaucoma, restenosis, capillary proliferation in atherosclerotic plaques and osteoporosis; and cancer associated disorders, such as solid tumors, solid tumor metastases, angiofibromas, retrolental fibroplasia, hemangiomas, Kaposi's sarcoma and the like cancers which require neovascularization to support tumor growth. Other suitable tumors include melanoma, carcinoma, sarcoma, fibrosarcoma, glioma and astrocytoma.

Thus, methods which inhibit angiogenesis in a diseased tissue treat and ameliorate symptoms of the disease and, depending upon the disease, can contribute to a cure.

In one embodiment, the present invention contemplates a method for inhibition of angiogenesis in a mammalian, e.g. human, tissue by administration of a denatured collagen type-IV selective antagonist.

As described herein, any of a variety of tissues, or organs comprised of organized tissues, can support angiogenesis in disease conditions including skin, muscle, gut, connective tissue, joints, bones and the like tissue, in which blood vessels can invade upon angiogenic stimuli. Tissue, as used herein, encompasses all bodily fluids, secretions and the like, such as, for example, serum, blood, cerebrospinal fluid, plasma, urine, synovial fluid, vitreous humor.

Thus, in one related embodiment, the tissue to be treated is an inflamed tissue and the angiogenesis to be inhibited is inflamed tissue angiogenesis where there is neovascularization of inflamed tissue. In this class, the method contemplates inhibition of angiogenesis in arthritic tissues (e.g., such as in a patient with chronic articular rheumatism), in immune or non-immune inflamed tissues, (e.g., in psoriatic tissue).

In another embodiment, the tissue to be treated is a retinal tissue of a patient with diabetic retinopathy, macular degeneration or neovascular glaucoma and the angiogenesis to be inhibited is retinal tissue angiogenesis where there is neovascularization of retinal tissue.

Restenosis is a process of smooth muscle cell (SMC) migration and proliferation at the site of previous stenosis in a blood vessel. The migration and proliferation of SMCs associated with blood vessels during restenosis is related to the process of angiogenesis which is inhibited by the present methods and compositions. The invention also contemplates inhibition of restenosis by inhibiting angiogenic related processes according to the present methods and compositions in a patient following a procedure to correct vascular stenosis. Accordingly, the methods and compositions disclosed herein can be used at sites of percutaneous transluminal coronary angioplasty, coronary artery bypass, peripheral artery bypass, mesenteric artery bypass, and carotid endarterectomy or angioplasty.

The dose ranges for the administration of the denatured collagen type-IV selective antagonist depend upon the form of the antagonist and its potency, and are amounts large enough to produce the desired effect in which angiogenesis and the disease symptoms mediated by angiogenesis are ameliorated. The dosage should not be so large as to cause adverse side effects such as hyperviscosity syndromes, pulmonary edema, congestive heart failure, and the like. Generally, the dose will vary with the age, condition, sex and extent of the disease in the patient and can be determined by one of skill in the art. The dose also can be adjusted by the physician in the event of any complication.

Potency of a denatured collagen type-IV selective antagonist can be measured by a variety of means including, for example, inhibition of angiogenesis in the CAM assay, or in the in vivo rabbit eye assay, in the in vivo chimeric mouse: human assay as discussed herein.

A therapeutically effective amount of a denatured collagen type-IV antagonist of this invention is typically an amount of peptide such that when administered in a pharmaceutically acceptable composition is sufficient to achieve a plasma concentration of from about 0.1 microgram (μg) per milliliter (ml) to about 200 μg/ml, preferably from about 1 μg/ml to about 150 μg/ml. Based on a polypeptide having a mass of about 500 grams per mole, the preferred plasma concentration in molarity is from about 2 micromolar (μM) to about 5 millimolar (mM) and preferably about 100 μM to 1 mM polypeptide antagonist. Stated differently, the dose per body weight can vary from about 0.1 mg/kg to about 300 mg/kg, and preferably from about 0.2 mg/kg to about 200 mg/kg, in one or more dose administrations daily, for one or several days.

Denatured collagen type-IV selective antagonists can be administered, for example, parenterally, by injection, or by gradual infusion over time. A preferred mode of administration for preventing angiogenesis is by intravenous administration of therapeutic compositions containing one or more of the biologically active agents of the present invention. Thus, antagonists and derivatives thereof can be administered intravenously, intraperitoneally, intramuscularly, subcutaneously, intracavity, transdermally, topically, intraocularly, orally, intranasally and can be delivered by peristaltic means. The therapeutic compositions of this invention may be administered intravenously, as by injection of a unit dose, for example.

In a preferred embodiment, the denatured collagen type-IV selective antagonist is administered in a single intravenous dose.

The compositions are administered in a manner compatible with the dosage formulation, and in a therapeutically effective amount. The quantity to be administered and timing depends on the patient to be treated, capacity of the patient's system to utilize the active ingredient, and degree of therapeutic effect desired. Precise amounts of active ingredient required to be administered depend on the judgment of the physician and are peculiar to each individual. However, suitable dose ranges for systemic application are disclosed herein and depend on the route of administration. Suitable regimes for administration also are variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

Inhibition of angiogenesis and tumor regression may occur as early as 7 days after the initial administration of the antagonist. Preferably, administration of antagonist is repeated resulting in tissue exposure to the antagonist for between 7 days and 6 weeks, more preferably between about 14 and 28 days.

For inhibition of restenosis, the denatured collagen type-IV selective antagonist is typically administered after the stenosis-relieving procedure for from about 2 to about 28 days, and more typically for about the first 14 days following the procedure.

Therapeutic Compositions

The present invention contemplates therapeutic compositions useful for practicing the therapeutic methods described herein. Therapeutic compositions of the present invention contain a pharmaceutically acceptable carrier together with a denatured collagen type-IV selective antagonist as described herein, dissolved or dispersed therein as an active ingredient. In a preferred embodiment, the therapeutic denatured collagen type-IV selective antagonist composition is not immunogenic when administered to a mammal or human patient for therapeutic purposes. One especially preferred denatured collagen type-IV selective antagonist is CLK peptide. Another preferred denatured collagen type-IV selective antagonist is SLK peptide. Another preferred denatured collagen type-IV selective antagonist is KGGCLK peptide.

The preparation of a pharmacological composition that contains active ingredients dissolved or dispersed therein is well understood in the art and need not be limited based on formulation. Typically such compositions are prepared as injectables either as liquid solutions or suspensions, however, solid forms suitable for solution, or suspensions, in liquid prior to use also can be prepared. The preparation also can be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups also can be derived from inorganic bases such as, for example, sodium, potassium, 3 ammonium, calcium or ferric hydroxides, and such organic bases as isopropylamine, trimethylamine, 2-ethylamino ethanol, histidine, procaine and the like. Particularly preferred are the salts of TFA and HCl.

Pharmaceutically acceptable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions also can contain liquid phases in addition to and to the exclusion of water. Exemplary of such additional liquid phases are glycerin, vegetable oils such as cottonseed oil, and water-oil emulsions.

A therapeutic composition contains an angiogenesis-inhibiting, tumor growth-inhibiting, or metastasis-inhibiting amount of a denatured collagen type-IV selective antagonist of the present invention, formulated to contain 0.01 to 90 weight percent of antagonist per weight of total therapeutic composition. A preferred therapeutic composition formulation contains 0.05 to 50 weight percent of antagonist per weight of total therapeutic composition. A most preferred therapeutic composition formulation contains 0.1 to 20 weight percent of antagonist per weight of total therapeutic composition. A weight percent is a ratio by weight of inhibitor to total composition. Thus, for example, 0.1 weight percent is 0.1 grams of inhibitor per 100 grams of total composition.

Detection Methods

Denatured collagen type-IV antagonists of the invention also are suitable for detection of angiogenesis, tumor growth, arthritis or other diseases or conditions associated with cellular interaction with denatured collagen type-IV in tissues. Such methods of detection may be used ex vivo and in vivo. An ex vivo method, for example, is the detection of angiogenesis, tumor growth or metastasis in a biopsy specimen.

Binding of detectably labeled denatured collagen selective antagonists to target tissue can be detected either directly or indirectly. Direct detection can be preformed on said antagonists comprising a detectable label such as a fluorochrome, a radioactive tag, paramagnetic heavy metal or diagnostic dye.

Indirect detection is performed using a detectable secondary reagent that interacts with the denatured collagen type-IV selective antagonist. A detectably labeled antibody that recognizes said antagonist can be used, for example, to visualize the location of the antagonist. Other methods of indirect detection are also known to those of ordinary skill in the art.

In vivo imaging methods permit the detection of a labeled antagonist that specifically binds to denatured collagen type-IV in the subject's body. The labeled antagonist is administered to a patient e.g., intravenously or intramuscularly. In vivo detection methods include magnetic resonance spectroscopy, positron-emission tomography (PET) and single photon emission tomography (SPECT). For purposes of in vivo imaging, the type of detection instrument available is a major factor in selecting a given label. For instance, radioactive isotopes and paramagnetic isotopes are particularly suitable for in vivo imaging. The type of instrument used will guide the selection of the radionuclide. For instance, the radionuclide chosen must have a type of decay which is detectable for a given type of instrument. However, any conventional method for visualizing diagnostic imaging can be utilized in accordance with this invention. In one embodiment, a radionuclide may be bound to an antibody either directly or indirectly by using an intermediary functional group. Intermediary functional groups which are often used to bind radioisotopes which exist as metallic ions to antibody are diethylenetriaminepentaacetic acid (DTPA) and ethylene diaminetetracetic acid (EDTA). Examples of metallic ions suitable as radioactive isotopes are $^{99}$mTc, $^{123}$I, $^{131}$I, $^{111}$In, $^{131}$I, $^{97}$Ru, $^{67}$Cu, $^{67}$Ga, $^{125}$I, $^{68}$Ga, $^{72}$As, $^{89}$Zr, and $^{201}$Tl. Examples of paramagnetic isotopes, particularly useful in Magnetic Resonance Imaging ("MRI"), include $^{157}$Gd, $^{55}$Mn, $^{162}$Dy, $^{52}$Cr, and $^{56}$Fe.

EXAMPLES

The following Examples illustrate the invention, but are not limiting.

Example 1

Generation of Peptides that Specifically Bind to Denatured Collagen Type-IV Epitopes Subtractive phage display was used to generate peptides that specifically bind to denatured collagen type-IV. Peptide were expressed as a fusion with a coat protein of a bacteriophage on the surface of a virion. Panning was carried out by incubating a library of phage-displayed peptides with a microtiter plate coated with the target (native collagen type-IV in wells 1-4, denatured collagen type-IV in well 5), washing away the unbound phage, and eluting the specifically-bound phage. The eluted phage was taken through repeated panning to enrich the pool in favor of binding sequences.

On day one, collagen type-IV at a concentration of 25 µg/ml was dissolved in 0.1M $NaHCO_3$ (pH8.6) and then the solution was boiled for 15 minutes, thereby yielding thermally denatured collagen. Next, the solution was cooled to room temperature.

100 microliters of native collagen type-IV (unboiled) was added to four wells (Nunc-Immuno™ Maxisorp™ available from Nalge Nunc International, Rochester, N.Y.) and 100 microliters of denatured collagen type-IV (boiled) was added to a fifth well. The plate was swirled repeatedly until its surface was wet. The plate, with its top sealed, was incubated overnight at a temperature of 4° C. with a gentle agitation.

On day two, 10 ml of LB/tet medium was inoculated with a single colony of ER2738 *E. coli* strain. LB/tet medium was prepared as follows: A liter of LB medium was prepared from 10 g/l of Bacto-tryptone and 5 g/l NaCl. The mixture was autoclaved for 15 minutes at 121° C. and then stored at room temperature. Tetracycline stock was prepared using 20 mg/ml of tetracycline in ethanol, which was stored at minus 20° C. in the dark, and then vortexed prior to use. LB/tet plates were prepared from LB medium and 15 g/l agar, which was autoclaved for 15 minutes at 121° C. and cooled to less than 70° C. One ml of tetracycline stock was then added and the mixture was poured onto the plates. The plates were stored at 4° C. in the dark.

Coating solution was poured off the first well and the well was washed twice with TBST (TBS+0.1% (v/v) Tween-20). TBS was prepared from 50 mM Tris-HCl (pH 7.5) and 150 mM NaCl, which was autoclaved for 15 minutes at 121° C. and stored at room temperature.

Next, $2 \times 10^{11}$ phage (10 microliter of the original library, obtained from New England Bio Labs, Inc.) was diluted with 100 microliters of TBST and pipetted onto the first well. The first well was then rocked gently for 60 minutes at 4° C.

The coating solution of the second well was poured off and the well was washed twice with TBST. Supernatant from the first well was then pipetted onto the second well. The second well was rocked gently for 60 minutes at 4° C.

The coating solution of the third well was poured off and the well was washed twice with TBST. Supernatant from the second well was then pipetted onto the third well. The third well was rocked gently for 60 minutes at 4° C.

The coating solution of the fourth well was poured off and the well was washed twice with TBST. Supernatant from the third well was then pipetted onto the fourth well. The fourth well was rocked gently for 60 minutes at 4° C.

The coating solution of the fifth well was poured off and the well was filled with blocking buffer (0.1M $NaHCO_3$ (pH 8.6), 5 mg/ml BSA, 0.02% $NaN_3$, filter sterilized and stored at 4° C.). Next, the fifth well was incubated for 60 minutes at 4° C. The blocking buffer solution was then discarded and the fifth well was washed six times with TBST. Supernatant from the fourth well was then pipetted onto the fifth well and the fifth well was incubated for 60 minutes at room temperature. Next, the solution was poured off the fifth well and the fifth well was washed ten times with TBST.

The phage bound to the fifth plate was eluted with 0.2M glycine-HCl (pH 2.2). Following elution, the phage was amplified and titrated. The phage was then used for the next round of panning. The process of day two was repeated three times, each time using the phage produced at the end of the previous run.

The final step was isolation and identification of the peptides by sequence, which yielded CLK and SLK peptides.

Example 2

Peptide Antagonists of Denatured Collagen Type-IV Blocked Tumor Cell Adhesion to Denatured Collagen Type-IV In vitro cell adhesion assays were conducted to determine whether the CLK and SLK peptides bind to functional epitopes within denatured collagen type-IV that regulate cellular adhesion. Non-tissue culture treated 48-well plates were coated with denatured collagen type-IV Human melanoma cells M21 (Scripps Research Institute, La Jolla, Calif.) were allowed to attach to the coated wells in the presence or absence of the synthetic peptides CLK, SLK, and SDR, each peptide was at a concentration of 250 µg/ml. SDR peptide is a commercially available peptide that was used as a control (QED Bioscience, Inc., San Diego, Calif.).

Human denatured collagen type-IV (25 µg/ml) was immobilized on 48-well nontissue culture treated plates. Wells were washed and incubated with 1% BSA (bovine serum albumin) in PBS (phosphate-buffered saline) for one hour at 37° C. Subconfluent HUVECs (human umbilical vein endothelial cells) were harvested, washed, and resuspended in adhesion buffer containing RPMI-1640 medium, 1 mM $MgCl_2$, 0.2 mM $MnCl_2$, and 0.5% BSA. HUVECs ($10^5$) were resuspended in 200 µl of the adhesion buffer in the presence or absence of each of the synthetic peptides and were added to each well and allowed to attach for 30 minutes at 37° C. The unattached cells were removed and the attached cells were stained for 10 minutes with crystal violet as described by Petitclerc, et al. (1999) Integrin αvβ3 promotes M21 melanoma growth in human skin by regulating tumor cell survival. Cancer Res. 59:2724-2730. The wells were washed three times with PBS and cell-associated crystal violet was eluted by addition of 100 µl of 10% acetic acid. Cell adhesion was quantified by measuring the optical density of eluted crystal violet at a wavelength of 600 nm.

Figure 1:
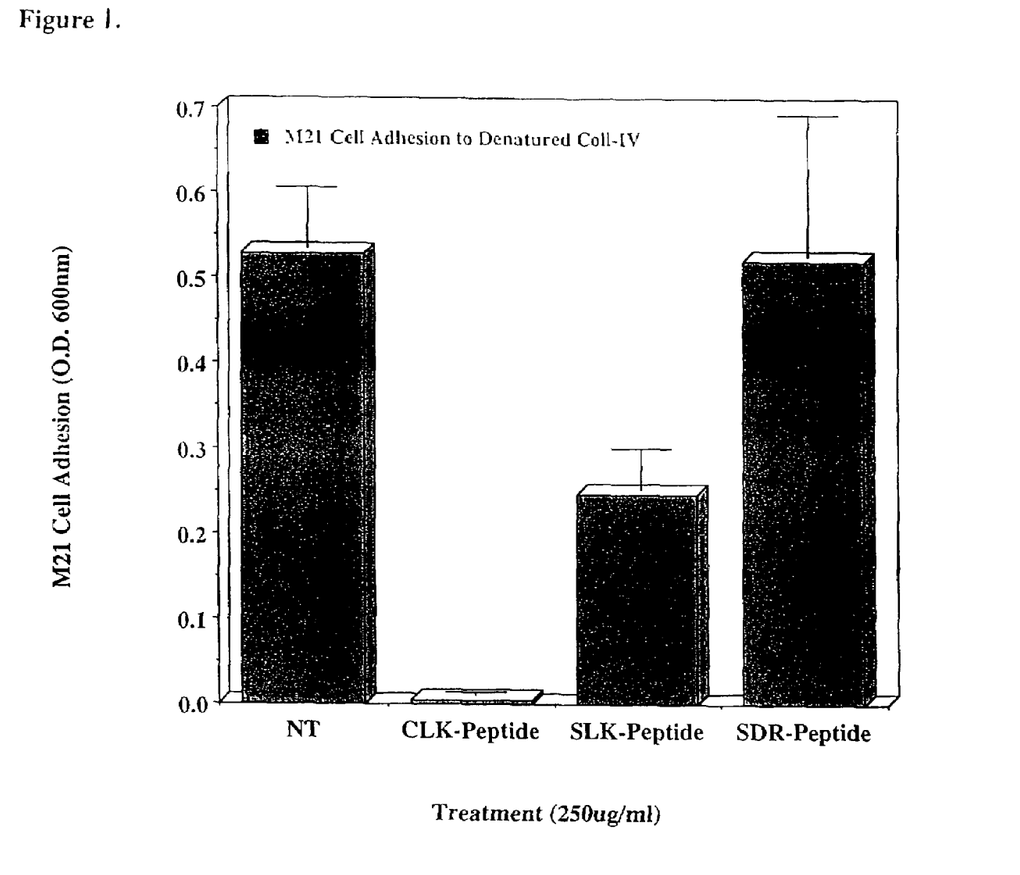
FIG. 1 is a chart which illustrates M21 human melanoma cell adhesion to untreated denatured type-IV collagen (NT), CLK-peptide treated denatured collagen type-IV, SLK-peptide treated denatured collagen type-IV, and SDR-peptide treated denatured collagen type-IV.

CLK-peptide blockade of melanoma cell adhesion exceeded 95% (FIG. 1). SLK-peptide blocked melanoma cell adhesion by about 50%.

Example 3

CLK-Peptide Blocked B16 Melanoma Cell Adhesion to Denatured Collagen Type-IV Non-tissue culture treated 48-well plates were coated with either native (triple helical) or denatured collagen type-IV.

Figure 2:
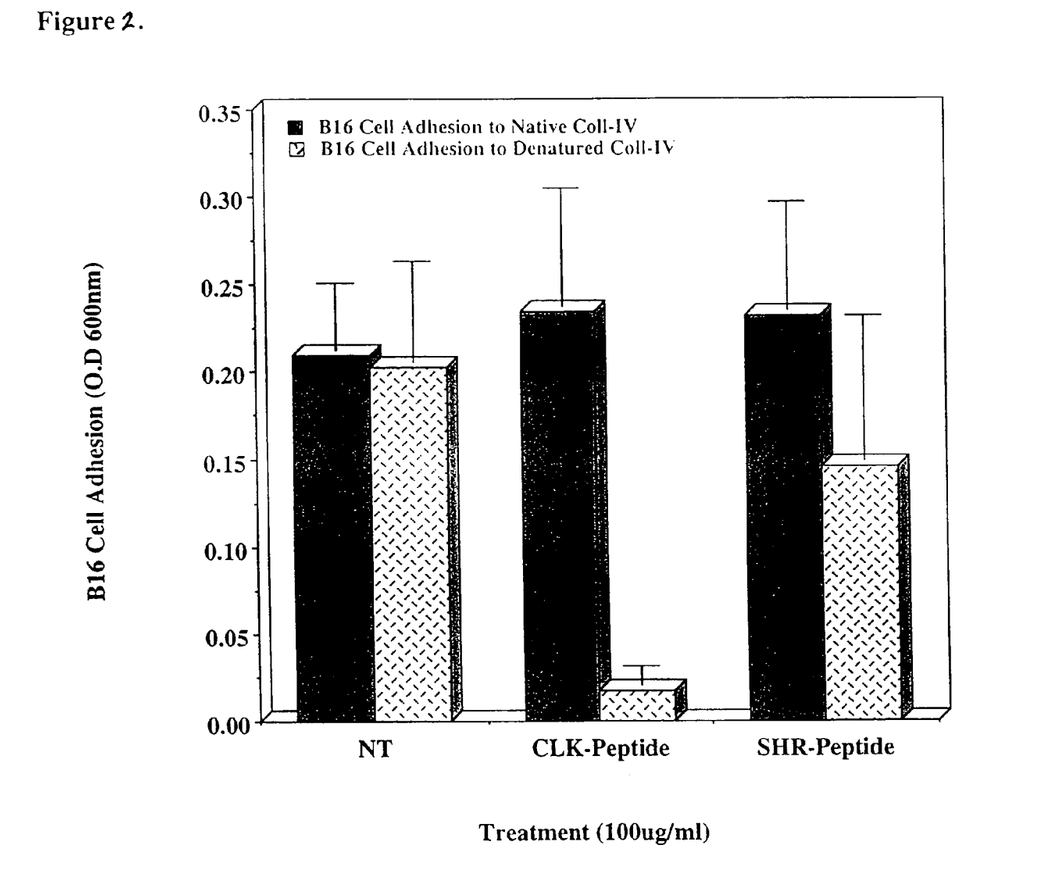
FIG. 2 is a chart which illustrates B16 murine melanoma cell adhesion to untreated denatured collagen type-IV (NT), CLK-peptide treated denatured collagen type-IV, and SHR-peptide treated denatured collagen type-IV.
Figure 3:
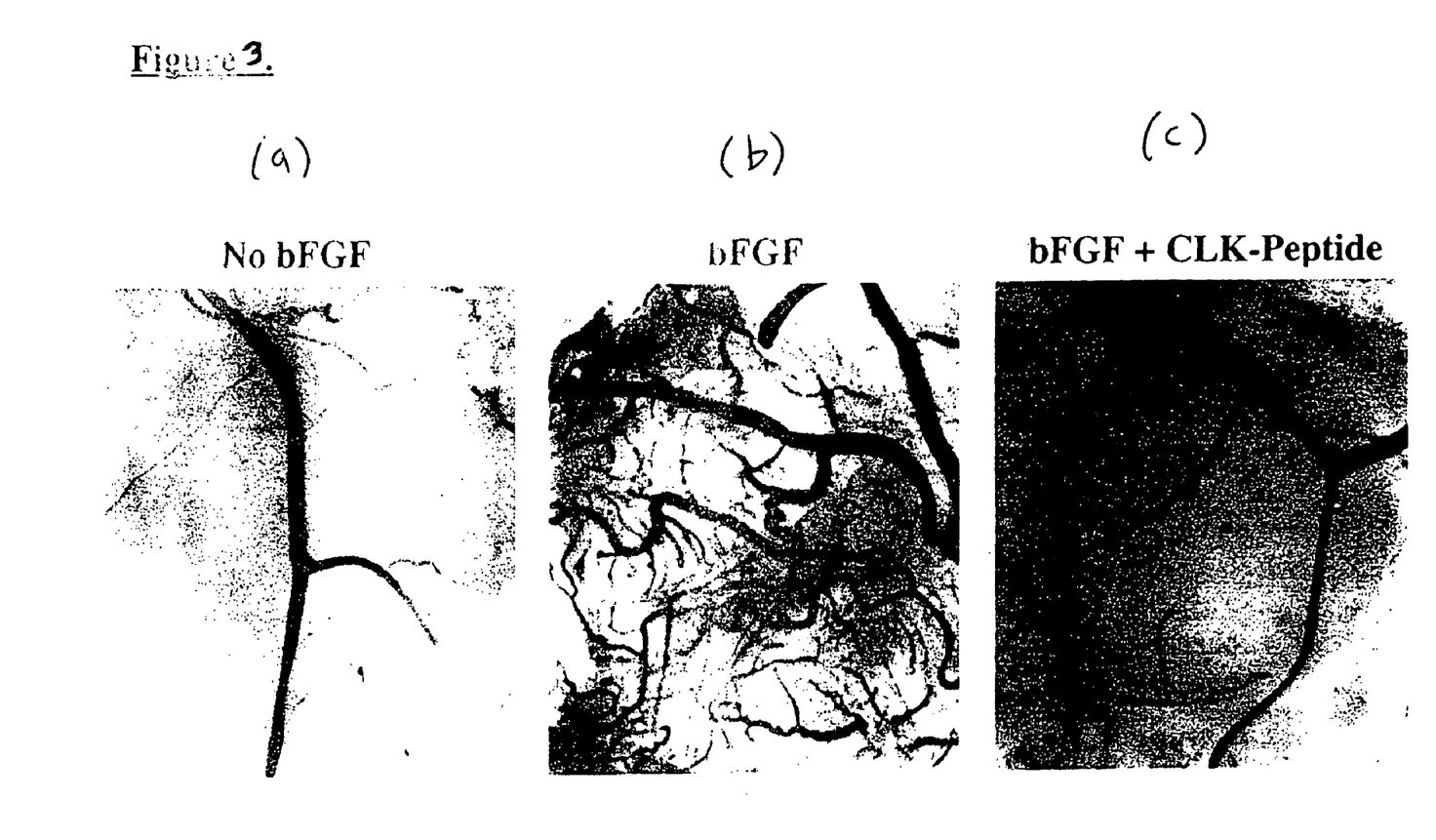

Metastatic B16 murine melanoma cells were allowed to attach to the coated wells in the presence or absence of either CLK or SHR (control) peptide. CLK-peptide blockade of B16 cell adhesion to denatured type-IV collagen exceeded 95% (FIG. 2). CLK-peptide had little effect on B16 melanoma cell adhesion to native collagen type-IV.

Example 4

CLK-Peptide Blocked bFGF-Induced Angiogenesis in the Chick CAM Model

Figure 4:
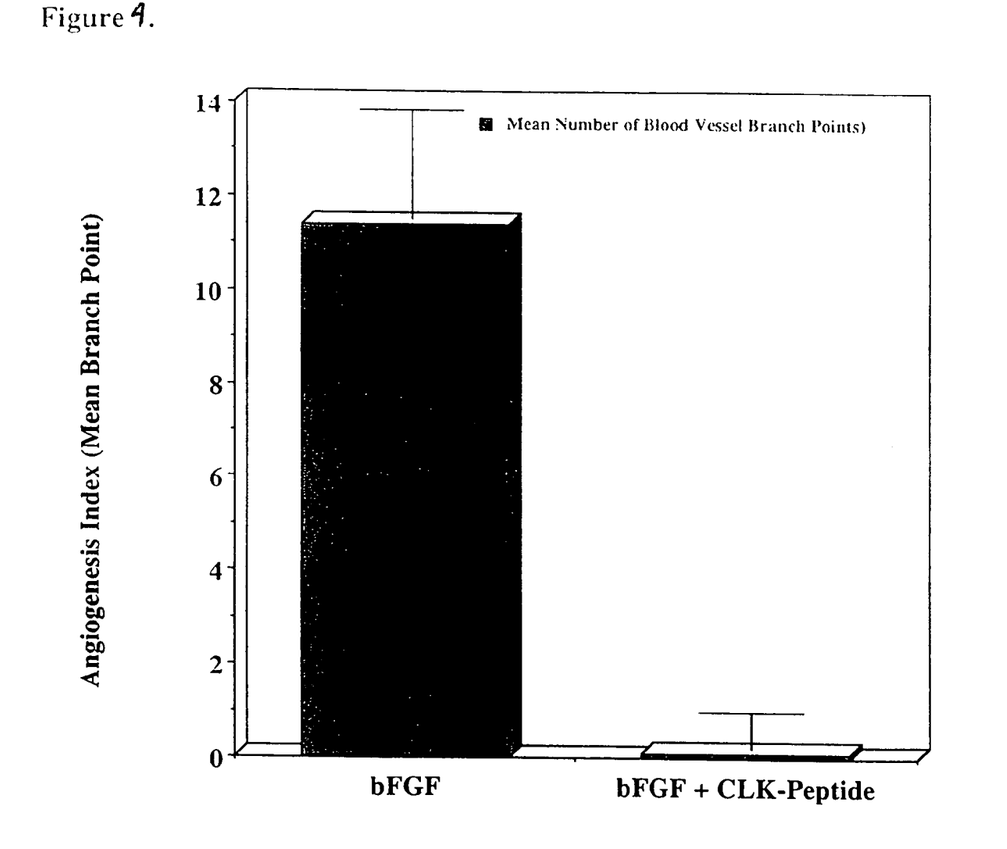
FIG. 4 is a chart which illustrates quantification of CAM angiogenic blood vessels following bFGF-induced angiogenesis without subsequent CLK-peptide treatment and CAM angiogenic blood vessels following bFGF-induced angiogenesis with subsequent CLK-peptide treatment.

Angiogenesis was induced within the chorioallantoic membrane (CAM) of 10-day old chick embryos with bFGF. Twenty-four hours later, 8-10 of the embryos were treated with a single intravenous injection of CLK-peptide (100 ug/embryo). At the end of a 3-day incubation period, the CAM tissues were removed for analysis. The injection of CLK-peptide resulted in a dramatic reduction in the number of branching vessels within the confined area of the filter disc. (FIGS. 3(a),(b),(c)) The single injection of CLK-peptide inhibited bFGF by greater than 95%. (FIG. 4) No adverse effects were noted following injection of the peptide. Eight to ten chick embryos were tested in each of the two groups, and the experiment was repeated three times for a total of 24-30 chick embryos tested.

Example 5

CLK-Peptide Inhibited B16 Melanoma Metastasis In Vivo

Figure 5:
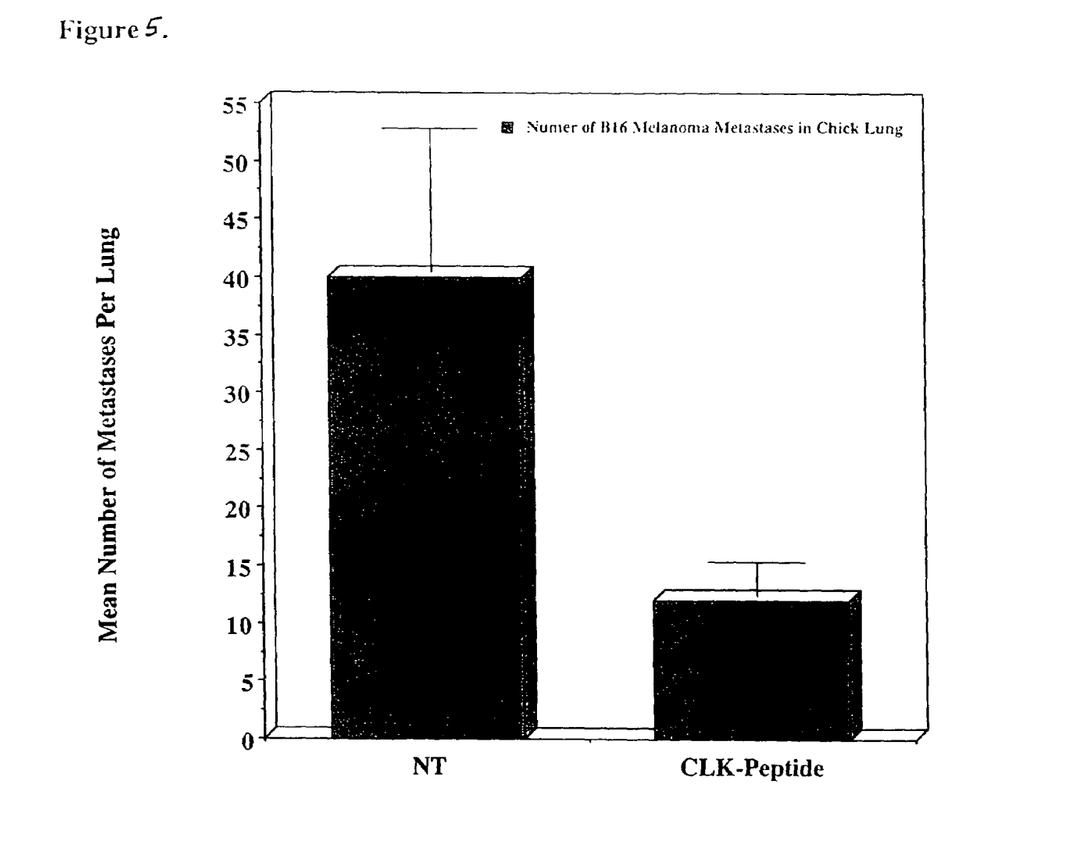
FIG. 5 is a chart, which illustrates quantification of B 16 melanoma metastases on chick embryo lungs untreated with CLK-peptide (NT) and chick embryo lungs treated with CLK-peptide.

Twelve-day old chick embryos (obtained from SPAFAS, North Franklin, Conn.) were injected intravenously with metastatic B16 melanoma cells (Chambers, et al. (1992) J. Natl. Cancer Inst., Vol. 84:797-803) in the presence or absence of CLK-peptide (100 ug/embryo). For each experiment, eight to ten chicks were tested under each set of conditions, and the experiment was repeated three times. The embryos were incubated for 7 days and then sacrificed. The chick lungs were analyzed for metastasis. B16 melanoma metastases appeared as discrete black lesions. The metastases were quantified by counting the B16 tumor lesions on the surface of the chick lungs for the CLK and no-CLK groups. B16 melanoma metastasis was inhibited by about 70% in the CLK group as compared to the no-CLK group. (FIG. 5)

Example 6

Treatment of a Patient with Metastatic Breast Cancer

A 60 kilogram patient with breast cancer metastatic to the liver has blood drawn for liver function tests. The patient undergoes an abdominal CT scan in order to note the size and number of the liver metastases. The patient's overall medical condition is assessed by a health professional using physical examination; blood tests such as a complete blood count, BUN, and creatinine; and EKG.

A CLK-peptide dose of 9000 milligrams is calculated by multiplying the patient's weight (60 kilograms) by the dose per body weight (150 milligrams per kilogram). The CLK-peptide dose is mixed in aqueous solution and administered intravenously through a peripheral vein catheter over a 2 hour period. Following infusion of CLK-peptide, the patient is monitored for 2 hours by a health professional for the appearance of adverse effects. In the absence of such effects, the patient is discharged home.

Two weeks following CLK-peptide infusion, the patient has repeat liver function tests and CT scan. Lowering of the liver function test values may be indicative of tumor metastases regression. CT scan visualization of decreased size and/or number of metastases is indicative of successful treatment of the metastases.

All patents and publications which are cited in the body of the instant specification are hereby incorporated by reference in their entirety.

It is also to be appreciated that the foregoing description of the invention has been presented for purposes of illustration and explanation and is not intended to limit the invention to the precise manner of practice herein. It is to be appreciated therefore, that changes may be made by those skilled in the art without departing from the spirit of the invention and that the scope of the invention should be interpreted with respect to the following claims.

We claim:

1. A selective antagonist to denatured collagen type-IV wherein said antagonist is a peptide comprising the core amino acid sequence SEQ ID NO. 1: L-K-Q-N-G-G-N-F-S-L.

2. The antagonist of claim 1 wherein the binding affinity of the antagonist to denatured type-IV collagen is substantially greater than the binding affinity of said antagonist to native collagen type-IV.

3. The antagonist of claim 1 wherein the binding affinity of the antagonist to denatured type-IV collagen is 100-fold greater than the binding affinity of said antagonist to native collagen.

4. The antagonist of claim 1 wherein the antagonist inhibits cellular interaction with denatured collagen type-IV.

5. A pharmaceutical composition comprising an antagonist according to claim 1 and a pharmaceutically acceptable excipient.

6. The pharmaceutical composition of claim 5 wherein the composition comprises a cytotoxic agent.

7. The pharmaceutical composition of claim 5 wherein the composition comprises a radioactive material.

8. The pharmaceutical composition of claim 5 wherein the composition comprises a cytostatic agent.

9. An antagonist selective for denatured collagen type-IV, wherein said antagonist is a polypeptide comprising the core amino acid sequence SEQ ID NO. 1: L-K-Q-N-G-G-N-F-S-L.

* * * * *

UNITED STATES PATENT AND TRADEMARK OFFICE
CERTIFICATE OF CORRECTION

| | | |
|---|---|---|
| PATENT NO. | : 7,601,694 B2 | Page 1 of 1 |
| APPLICATION NO. | : 10/782728 | |
| DATED | : October 13, 2009 | |
| INVENTOR(S) | : Peter C. Brooks | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 924 days.

Signed and Sealed this

Twenty-eighth Day of September, 2010

David J. Kappos
*Director of the United States Patent and Trademark Office*

```
                           SEQUENCE LISTING

<160> NUMBER OF SEQ ID NOS: 4

<210> SEQ ID NO 1
<211> LENGTH: 10
<212> TYPE: PRT
<213> ORGANISM: artificial sequence
<220> FEATURE:
<223> OTHER INFORMATION: denatured collagen type-IV selective antagonist

<400> SEQUENCE: 1

Leu Lys Gln Asn Gly Gly Asn Phe Ser Leu
1               5                   10

<210> SEQ ID NO 2
<211> LENGTH: 12
<212> TYPE: PRT
<213> ORGANISM: artificial sequence
<220> FEATURE:
<223> OTHER INFORMATION: denatured collagen type-IV selective antagonist

<400> SEQUENCE: 2
```

```
Cys Leu Lys Gln Asn Gly Gly Asn Phe Ser Leu Gly
1               5                   10

<210> SEQ ID NO 3
<211> LENGTH: 12
<212> TYPE: PRT
<213> ORGANISM: artificial sequence
<220> FEATURE:
<223> OTHER INFORMATION: denatured collagen type-IV selective antagonist

<400> SEQUENCE: 3

Ser Leu Lys Gln Asn Gly Gly Asn Phe Ser Leu Cys
1               5                   10

<210> SEQ ID NO 4
<211> LENGTH: 18
<212> TYPE: PRT
<213> ORGANISM: artificial sequence
<220> FEATURE:
<223> OTHER INFORMATION: denatured collagen type-IV selective antagonist

<400> SEQUENCE: 4

Lys Gly Gly Cys Leu Lys Gln Asn Gly Gly Asn Phe Ser Leu Gly Gly
1               5                   10                  15

Lys Ala
```